(12) United States Patent
Gore et al.

(10) Patent No.: US 9,150,524 B2
(45) Date of Patent: Oct. 6, 2015

(54) PURE INTERMEDIATE

(75) Inventors: Vinayak Govind Gore, Maharashtra (IN); Vinay Kumar Shukla, Maharashtra (IN); Sandeep Mekde, Maharashtra (IN); Suresh Hasbe, Maharashtra (IN); Shreyas Bhandari, Maharashtra (IN); Dhananjay Shinde, Maharashtra (IN); Madhukar Shaligram Patil, Maharashtra (IN)

(73) Assignee: Generics [UK] Limited, Albany Gate, Darkes Lane, Potters Bar, Hertfordshire (GB)

( * ) Notice: Subject to any disclaimer, the term of this patent is extended or adjusted under 35 U.S.C. 154(b) by 0 days.

(21) Appl. No.: 13/818,815

(22) PCT Filed: Aug. 26, 2011

(86) PCT No.: PCT/GB2011/051611
§ 371 (c)(1),
(2), (4) Date: Apr. 3, 2013

(87) PCT Pub. No.: WO2012/025762
PCT Pub. Date: Mar. 1, 2012

(65) Prior Publication Data
US 2013/0203826 A1 Aug. 8, 2013

(30) Foreign Application Priority Data
Aug. 27, 2010 (IN) .................. 2395/MUM/2010

(51) Int. Cl.
*C07D 249/08* (2006.01)
*A61K 31/4196* (2006.01)

(52) U.S. Cl.
CPC .......... *C07D 249/08* (2013.01); *A61K 31/4196* (2013.01)

(58) Field of Classification Search
CPC .................................................. C07D 249/08
USPC ..................................................... 548/262.2
See application file for complete search history.

(56) References Cited

U.S. PATENT DOCUMENTS

| | | | |
|---|---|---|---|
| 4,978,672 | A | 12/1990 | Bowman et al. |
| 2007/0066831 | A1 | 3/2007 | MacDonald et al. |

FOREIGN PATENT DOCUMENTS

| | | | |
|---|---|---|---|
| JP | 62-212369 | A | 9/1987 |
| JP | 2008-516005 | A | 5/2008 |
| JP | 2009-530256 | A | 8/2009 |
| WO | WO 03/050093 | A | 6/2003 |
| WO | WO 2004/076409 | A2 | 9/2004 |
| WO | WO 2005/047269 | A1 | 5/2005 |
| WO | WO 2007/039912 | A1 | 4/2007 |
| WO | WO 2007/054964 | A2 | 5/2007 |
| WO | WO 2007/107733 | A1 | 9/2007 |
| WO | WO 2007/144896 | A1 | 12/2007 |
| WO | WO 2009/069140 | A1 | 6/2009 |
| WO | WO 2010/146391 | A1 | 12/2010 |
| WO | WO 2011/000396 | A1 | 1/2011 |

OTHER PUBLICATIONS

HCAPlus:STN Database Accession No. 145:124574, "Process for Preparation of Letrozole," XP002666936, 6 pages, (2006).
HCAPlus:STN Database Accession No. 147:427348, "Method for Preparation of Letrozole," XP002666937, 2 pages, (2007).
PCT International Preliminary Report on Patentability (Chapter I) of Mar. 5, 2013 for application PCT/GB2011/051611.
PCT International Search Report for application PCT/GB2011/051611 mailed Mar. 21, 2012.

*Primary Examiner* — Rebecca Anderson
*Assistant Examiner* — Karen Cheng
(74) *Attorney, Agent, or Firm* — Joe Liebeschuetz (Alston & Bird LLP)

(57) ABSTRACT

The present invention relates to an improved process for the preparation of Letrozole (I) and its synthetic intermediate 4-[(1-(1,2,4-triazoly)methyl]benzonitrile (III). In particular, it relates to a process to prepare Letrozole and its intermediate (III) substantially free from regioisomeric impurities. The present invention further relates to acid addition salts of 4-[(1-(1,2,4-triazoly)methyl]benzonitrile (III) such as the oxalate salt, and also to Letrozole (I), the intermediate (III) and salts thereof preparable by the processes of the present invention.

16 Claims, 4 Drawing Sheets

PURE INTERMEDIATE

CROSS-REFERENCE TO RELATED APPLICATIONS

This application is the U.S. National Stage of International Application PCT/GB2011/051611 filed Aug. 26, 2011, and which claims the benefit of India Patent Application No. 2395/MUM/2010, filed Aug. 27, 2010.

FIELD OF THE INVENTION

The present invention relates to an improved process for the preparation of Letrozole (I) and its synthetic intermediate 4-[(1-(1,2,4-triazolyl)methyl]benzonitrile (III). In particular, it relates to a process to prepare Letrozole and its intermediate (III) substantially free from regioisomeric impurities. The present invention further relates to acid addition salts of 4-[(1-(1,2,4-triazolyl)methyl]benzonitrile (III) such as the oxalate salt, and also to Letrozole (I), the intermediate (III) and salts thereof preparable by the processes of the present invention.

BACKGROUND OF THE INVENTION

Letrozole, chemically named as 4-[1-(4-cyanophenyl)-1-(1,2,4-triazol-1-yl)methyl)]-benzonitrile (I) is one of a new class of drugs, known as aromatase inhibitors, which function by reducing oestrogen levels in postmenopausal women as many breast cancers increase in size by utilising the hormone oestrogen. In women who have undergone the menopause, the main source of oestrogen is through the conversion of androgens (sex hormones produced by the adrenal glands) into oestrogen. The conversion process, which is known as aromatisation, happens mainly in the fatty tissues of the body and is catalysed by an enzyme called aromatase. Letrozole blocks this aromatisation process and reduces the amount of oestrogen in the body. Consequently, Letrozole is marketed as a type of hormonal therapy that is used in the treatment of breast cancer in women.

Letrozole and processes to prepare it were first described in U.S. Pat. No. 4,978,672. The synthesis of Letrozole proceeded via the reaction of intermediate 4-[(1-(1,2,4-triazolyl)methyl]benzonitrile (III) with 4-fluorobenzonitrile (IV) in the presence of a catalyst, potassium tert-butoxide. The preparation of intermediate (III) was achieved by the reaction of 4-bromomethylbenzonitrile with 1,2,4-triazole in a mixture of chloroform and acetonitrile at reflux, followed by the purification of the product (III) by column chromatography. It was found that during the preparation of intermediate (III), an undesired regioisomer, namely 4-[(1-(1,3,4-triazolyl)-methyl]benzonitrile (V), was formed in about 20-25% yield. Consequently, this leads to an uneconomical loss of yield and to a difficult and inconvenient purification of intermediate (III), which was required to remove the regioisomeric impurity (V). In addition, complete purification was not possible and the impurity (V) was carried through the synthesis resulting in the formation of regioisomer (II) in the synthetic step to prepare Letrozole. As a consequence, the final purification of Letrozole had to involve the removal of impurity (II). These two purifications were very difficult and a substantial quantity of material was lost during the purifications by column chromatography. In addition, the removal of the impurities by column chromatography vastly increased the solvent consumption of the process and purification using column chromatography is not a practical approach for the industrial production of Letrozole or its intermediates.

Another process for the preparation of Letrozole, disclosed in patent application WO 2005/047269, recognised that the removal of the undesired regioisomers by column chromatography is a problem. The disclosed method for separation of the unwanted impurity (V) from the intermediate (III) is by preparation of its hydrochloride salt, which is relatively less soluble in the solvents dichloromethane and chloroform, and separation by filtration while the desired product hydrochloride salt remains in solution. The desired intermediate is then isolated as the free base and purified by removal of solvent to afford the intermediate (III) with a purity of 99.7% by HPLC. Although control of the isomeric purity was somewhat achieved by this method, the loss of significant quantities of the desired product (III) could not be avoided and this route is not attractive for commercial production, particularly as the process involved the use of several solvents and a lengthy process for the separation of the undesired isomer which makes the process less feasible for scale-up. In addition, regioisomeric impurity (V) could still be detected in the product (III) and, as described above, this is a great disadvantage in the preparation of Letrozole as impurity (V) is converted into regioisomeric impurity (II) which is very difficult to remove from Letrozole on a commercial scale.

A regio specific preparation of the intermediate 4-[(1-(1,2,4-triazolyl)methyl]-benzonitrile (III), was disclosed in patent application WO 2004/076409. The disclosed process afforded intermediate (III) significantly free from its regioisomeric impurity by using the 4-amino-derivative of 1,2,4-triazole so that regioselectivity in the reaction could be achieved. The desired intermediate 4-[(1-(1,2,4-triazolyl)methyl]benzonitrile (III) was obtained by de-amination of its 4-amino derivative with sodium nitrite and concentrated hydrochloric acid. However, this process suffers from the disadvantages that extra steps are involved in the synthesis and toxic nitrous acid is formed during the de-amination reaction. Consequently, it is not a very safe and feasible approach for the commercial production of Letrozole. In addition, this process, although reducing the level of 1,3,4-triazolyl isomeric impurity, did not totally eliminate the formation of the impurity.

Similar approaches to reducing the regioisomeric impurity were discussed in patent applications WO 2007/039912 and US 2007/0066831, wherein the reaction of an alkali metal (preferably sodium or potassium) salt of 1,2,4-triazole with α-bromo-tolunitrile (4-bromomethylbenzonitrile) was disclosed. The alkali metal salt of 1,2,4-triazole was dissolved in a solvent such as NMP, DMAc, DMF, THF or a mixture thereof, and subsequently treated with 4-bromomethylbenzonitrile to afford intermediate (III). This process, although reducing the level of 1,3,4-triazolyl isomeric impurity, did not totally eliminate the formation of the impurity. In addition, the formation of the alkali salt of 1,2,4-triazole also increases the time cycle of the process due to the additional step. The process also required column chromatography for purification of the final product Letrozole, which again makes this process unfeasible for industrial application.

(T)

In another approach, disclosed in patent application, WO 2007/144896, a 4,4'-disubstituted diphenylmethane moiety was prepared and then the 1,2,4-triazole ring was introduced to afford Letrozole. The process involved the coupling of 4-fluorobenzonitrile (IV) with 4-tolunitrile in DMF using potassium tertiary butoxide as a catalyst. The resulting 4,4'-di(cyanophenyl)methane was brominated with N-bromosuccinimide to afford a bromomethyl intermediate, which was reacted with 1,2,4-triazole to afford Letrozole. However, formation of the 1,3,4-triazolyl isomeric impurity (II) could not be totally avoided and, in addition, the reaction of 4-tolunitrile and 4-fluorobenzonitrile also leads to significant formation of a tris-phenyl impurity (T) which is problematic to remove, particularly on a commercial scale.

Another process, disclosed in patent application, US 2005/0209294, describes the reaction of 4-bromomethylbenzonitrile with the Li, Na or K salt of 1,2,4-triazole in tetrahydrofuran or N,N-dimethylformamide at 10° C. The product, intermediate (III), was then purified by solvent crystallization using a solvent selected from a group comprising 2-propanol, toluene or diisopropyl ether. This process required one additional step to prepare the 1,2,4-triazole Li, Na or K salt and did not give a pure product.

A further process, disclosed in patent application WO2007/090464 A1, describes the preparation of intermediate (III) by reacting 1,2,4-triazole with a suspension of sodium hydride before further reaction with 4-bromomethylbenzonitrile. The reaction product was directly converted to Letrozole without further purification. Repetition of the process disclosed in this patent application gave inconsistent regioisomeric impurity levels in Letrozole and intermediate (III), giving around 90.0% purity at best. In addition, the use of sodium hydride also makes the process relatively unsafe on a commercial scale.

A process, disclosed in patent application WO 2007/054964 A2, describes the isolation of intermediate (III) by reacting 1,2,4-triazole with 4-bromomethyl-benzonitrile in 2-propanol using potassium carbonate as base. After completion of the reaction, the undesired regioisomer (V) was removed by making the hydrochloride salt of the crude reaction mixture followed by solvent extraction and then extraction of the product under alkaline conditions. Different extractions under various pH conditions to achieve the desired purity make the process lengthy and cumbersome and repetition of the process does not lead to intermediate (III) or Letrozole (I) free from their respective regioisomeric impurities.

A process, disclosed in patent application WO2007/107733 A1, includes the use of Caesium carbonate as a base and potassium iodide in catalytic quantity in the reaction of 1,2,4-triazole with 4-bromomethylbenzonitrile. In the reaction, $CsCO_3$, KI and 1,2,4-triazole were taken in acetone and a solution of 4-bromomethyl-benzonitrile in DCM was slowly added followed by refluxing of the reaction mixture. Isolation and purification of the desired isomer (III) was carried out by making the hydrochloride salt to afford product (III) in 99% of the desired isomeric purity.

Another process, disclosed in patent application WO 2009/069140 A1, describes the preparation of triazole intermediate (III) by addition of 1,2,4-triazole in small lots to a mixture of 4-bromomethylbenzonitrile and a base (such as sodium or potassium carbonate) in toluene at 50 to 110° C. The residue left after removal of the organic solvent was dissolved in ethyl acetate and washed with water. IPA-HCl solution was then added to adjust the pH to between 0 and 2. The purified triazole intermediate was liberated by basifying the hydrochloride salt to afford a product with 99.0% isomeric purity.

In all the acid/base purification methods discussed above, when repeated the regioisomeric purity of the desired isomer (III) or (I) was found to be 99.0% at best. The methods also required extraction with various solvents and/or column chromatography which makes the process less viable on a commercial scale.

Therefore the prior art processes described above for the preparation of Letrozole and its intermediates have major disadvantages with respect to the formation and removal of process related impurities; poor commercial viability due to the use of hazardous reactants; expensive, time consuming separation methods such as column chromatography; and/or low yields of the final product.

As the commercial production of Letrozole is of great importance and in view of the above disadvantages associated with the prior art there is a real need for alternative and improved processes for the preparation of Letrozole (I) and intermediate 4-[(1-(1,2,4-triazolyl)-methyl]benzonitrile (III) which do not involve multiple steps and further eliminate the need for cumbersome purification techniques, particularly for the removal of the regioisomers (II) and (V). The alternative processes must be economical and high yielding and provide Letrozole with a high degree of chemical purity.

The present process discloses a simple, economic and commercially viable process for the preparation of intermediate 4-[(1-(1,2,4-triazolyl)methyl]benzonitrile (III) and Letrozole (I) with 99.7% or more isomeric and chemical purity.

SUMMARY OF THE INVENTION

The difficulties encountered in the prior art for the preparation of highly pure Letrozole have been successfully overcome in the present invention by the preparation of highly pure intermediate 4-[(1-(1,2,4-triazolyl)methyl]benzonitrile (III) via its salt.

Therefore a first aspect of the present invention provides an acid addition salt of 4-[(1-(1,2,4-triazolyl)methyl]benzonitrile (III), wherein the acid is not hydrochloric acid.

A second aspect of the present invention provides an acid addition salt of 4-[(1-(1,2,4-triazolyl)methyl]benzonitrile (III), wherein the acid is an organic acid.

In one embodiment of either of the first or second aspects of the present invention, the acid has a p$K_a$ (relative to water) of more than −1. For example, the acid may have a p$K_a$ of about −0.5, 0, 1, 2 or 3 etc. Preferably the acid has a p$K_a$ (relative to water) of more than 0, and more preferably of more than 1.

As used herein, an "acid" may refer to any compound with a p$K_a$ (relative to water) of less than 10. Optionally, an "acid" may refer to any compound with a p$K_a$ of less than 5.

p$K_a$ values of acids are known in the art, for example from Table 8.1 on pages 250-2 of "Advanced Organic Chemistry" by J. March, 4th Ed., 1992.

Preferably, the acid is a carboxylic acid, such as a mono-, a di- or a tri-carboxylic acid.

Where the acid is a mono-carboxylic acid, preferably it is represented by the formula R$^1$COOH, wherein R$^1$ is selected from hydrogen or an optionally substituted alkyl, alkenyl, alkynyl, aryl, arylalkyl, arylalkenyl, arylalkynyl, alkylaryl, alkenylaryl or alkynylaryl group. Preferably R$^1$ is an optionally substituted alkyl or arylalkyl group.

More preferably R$^1$ is an optionally substituted $C_1$ to $C_{20}$ alkyl group, more preferably still R$^1$ is an optionally substituted $C_1$ to $C_{12}$ alkyl group. Most preferably, R$^1$ is an optionally substituted $C_1$ to $C_6$ alkyl group.

For the purposes of the present invention, an "allyl" group is defined as a monovalent saturated hydrocarbon, which may be straight-chained or branched, or be or include cyclic groups. An alkyl group may optionally include one or more heteroatoms N, O or S in its carbon skeleton. Examples of alkyl groups are methyl, ethyl, n-propyl, i-propyl, n-butyl, butyl, t-butyl and n-pentyl groups. Preferably an alkyl group is straight-chained or branched and does not include any heteroatoms in its carbon skeleton. Preferably an alkyl group is a $C_1$-$C_{12}$ alkyl group, which is defined as an alkyl group containing from 1 to 12 carbon atoms. More preferably an alkyl group is a $C_1$-$C_6$ alkyl group, which is defined as an alkyl group containing from 1 to 6 carbon atoms. An "alkylene" group is similarly defined as a divalent alkyl group.

An "alkenyl" group is defined as a monovalent hydrocarbon, which comprises at least one carbon-carbon double bond, which may be straight-chained or branched, or be or include cyclic groups. An alkenyl group may optionally include one or more heteroatoms N, O or S in its carbon skeleton. Examples of alkenyl groups are vinyl, allyl, but-1-enyl and but-2-enyl groups. Preferably an alkenyl group is straight-chained or branched and does not include any heteroatoms in its carbon skeleton. Preferably an alkenyl group is a $C_2$-$C_{12}$ alkenyl group, which is defined as an alkenyl group containing from 2 to 12 carbon atoms. More preferably an alkenyl group is a $C_2$-$C_6$ alkenyl group, which is defined as an alkenyl group containing from 2 to 6 carbon atoms. An "alkenylene" group is similarly defined as a divalent alkenyl group.

An "alkynyl" group is defined as a monovalent hydrocarbon, which comprises at least one carbon-carbon triple bond, which may be straight-chained or branched, or be or include cyclic groups. An alkynyl group may optionally include one or more heteroatoms N, O or S in its carbon skeleton Examples of alkynyl groups are ethynyl, propargyl, but-1-ynyl and but-2-ynyl groups. Preferably an alkynyl group is straight-chained or branched and does not include any heteroatoms in its carbon skeleton. Preferably an alkynyl group is a $C_2$-$C_{12}$ alkynyl group, which is defined as an alkynyl group containing from 2 to 12 carbon atoms.

More preferably an alkynyl group is a $C_2$-$C_6$ alkynyl group, which is defined as an alkynyl group containing from 2 to 6 carbon atoms. An "alkynylene" group is similarly defined as a divalent alkynyl group.

An "aryl" group is defined as a monovalent aromatic hydrocarbon. An aryl group may optionally include one or more heteroatoms N, O or S in its carbon skeleton. Examples of aryl groups are phenyl, naphthyl, anthracenyl and phenanthrenyl groups. Preferably an aryl group does not include any heteroatoms in its carbon skeleton. Preferably an aryl group is a $C_4$-$C_{14}$ aryl group, which is defined as an aryl group containing from 4 to 14 carbon atoms. More preferably an aryl group is a $C_6$-$C_{10}$ aryl group, which is defined as an aryl group containing from 6 to 10 carbon atoms. An "arylene" group is similarly defined as a divalent aryl group.

For the purposes of the present invention, where a combination of groups is referred to as one moiety, for example, arylalkyl, arylalkenyl, arylalkynyl, alkylaryl, alkenylaryl or alkynylaryl, the last mentioned group contains the atom by which the moiety is attached to the rest of the molecule. A typical example of an arylalkyl group is benzyl.

For the purposes of this invention, an optionally substituted alkyl, alkenyl, alkynyl, aryl, arylalkyl, arylalkenyl, arylalkynyl, alkylaryl, alkenylaryl or alkynylaryl group may be substituted with one or more of —F, —Cl, —Br, —I, —CF$_3$, —CCl$_3$, —CBr$_3$, —CI$_3$, —OH, —SH, —NH$_2$, —CN, —NO$_2$, —N$_3$, —COOH, —R$^\alpha$—O—R$^\beta$, —R$^\alpha$—S—R$^\beta$, —R$^\alpha$—SO—R$^\beta$, —R$^\alpha$—SO$_2$—R$^\beta$, —R$^\alpha$—SO$_2$—OR$^\beta$, —R$^\alpha$O—SO$_2$—R$^\beta$, —R$^\alpha$—SO$_2$—N(R$^\beta$)$_2$, —R$^\alpha$—NR$^\beta$—SO$_2$—R$^\beta$, —R$^\alpha$O—SO$_2$—OR$^\beta$, —R$^\alpha$O—SO$_2$—N(R$^\beta$)$_2$, —$R^\alpha$—$NR^\beta$—$SO_2$—$OR^\beta$, —$R^\alpha$—$NR^\beta$—$SO_2$—$N(R^\beta)_2$, —$R^\alpha$—$N(R^\beta)_2$, —$R^\alpha$—$N(R^\beta)_3^+$, —$R^\alpha$—$P(R^\beta)_2$, —$R^\alpha$—$Si(R^\beta)_3$, —$R^\alpha$—CO—$R^\beta$, —$R^\alpha$—CO—$OR^\beta$, —$R^\alpha O$—CO—$R^\beta$, —$R^\alpha$—CO—$N(R^\beta)_2$, —$R^\alpha$—$NR^\beta$—CO—$R^\beta$, —$R^\alpha O$—CO—$OR^\beta$, —$R^\alpha O$—CO—$N(R^\beta)_2$, —$R^\alpha$—$NR^\beta$—CO—$N(R^\beta)_2$, —$R^\alpha$—CS—$R^\beta$, —$R^\alpha$—CS—$OR^\beta$, —$R^\alpha O$—CS—$R^\beta$, —$R^\alpha$—CS—$N(R^\beta)_2$, —$R^\alpha$—$NR^\beta$—CS—$R^\beta$, —$R^\alpha O$—CS—$OR^\beta$, —$R^\alpha O$—CS—$N(R^\beta)_2$, —$R^\alpha$—$NR^\beta$—CS—$OR^\beta$, —$R^\alpha$—$NR^\beta$—CS—$N(R^\beta)_2$, —$R^\beta$, a bridging substituent such as —O—, —S—, —$NR^\beta$— or —$R^\alpha$—, or a π-bonded substituent such as =O, =S or =$NR^\beta$. In this context, —$R^\alpha$— is independently a chemical bond, a $C_1$-$C_{10}$ alkylene, $C_1$-$C_{10}$ alkenylene or $C_1$-$C_{10}$ alkynylene group. —$R^\beta$ is independently hydrogen, unsubstituted $C_1$-$C_6$ alkyl or unsubstituted $C_6$-$C_{10}$ aryl. Optional substituent(s) are preferably taken into account when calculating the total number of carbon atoms in the parent group substituted with the optional substituent(s). Preferably an optionally substituted alkyl, alkenyl, alkynyl, aryl, arylalkyl, arylalkenyl, arylalkynyl, alkylaryl, alkenylaryl or alkynylaryl group is not substituted with a bridging substituent. Preferably an optionally substituted alkyl, alkenyl, alkynyl, aryl, arylalkyl, arylalkenyl, arylalkynyl, alkylaryl, alkenylaryl or alkynylaryl group is not substituted with a π-bonded substituent. Preferably a substituted group comprises 1, 2 or 3 substituents, more preferably 1 or 2 substituents, and even more preferably 1 substituent.

Any optional substituent may be protected. Suitable protecting groups for protecting optional substituents are known in the art, for example from "Protective Groups in Organic Synthesis" by T. W. Greene and P. G. M. Wuts (Wiley-Interscience, 4$^{th}$ edition, 2006).

Preferably, where the acid is a mono-carboxylic acid, it is selected from formic acid, acetic acid, propionic acid or butyric acid.

In a preferred embodiment of either of the first or second aspects of the present invention, the acid is a di-carboxylic acid, such as an acid represented by the formula HOOC—$R^2$—COOH, wherein —$R^2$— is selected from a chemical bond or an optionally substituted alkylene, alkenylene, alkynylene, arylene, arylalkylene, arylalkenylene or arylalkynylene group. Preferably —$R^2$— is selected from a chemical bond or an optionally substituted alkylene, alkenylene, alkynylene, arylene group. More preferably —$R^2$— is selected from a chemical bond or an optionally substituted alkylene or alkenylene group. Most preferably —$R^2$— is selected from a chemical bond or an optionally substituted alkylene group.

For the purposes of the present invention, where a divalent combination of groups is referred to as one moiety, for example, arylalkylene, arylalkenylene, or arylalkynylene, the last mentioned group contains one atom by which the moiety is attached to the rest of the molecule and the first mentioned group contains the other atom by which the moiety is attached to the rest of the molecule.

In one embodiment of either of the first or second aspects of the present invention, —$R^2$— contains from 0 to 20 carbon atoms. Preferably —$R^2$— contains from 0 to 12 carbon atoms, more preferably from 0 to 6 carbon atoms. Most preferably —$R^2$— contains from 0 to 3 carbon atoms.

Where the acid is a di-carboxylic acid, optionally the di-carboxylic acid may be selected from oxalic acid, tartaric acid, succinic acid, fumaric acid, malic acid, maleic acid, malonic acid, hydroxysuccinic acid, hydroxymaleic acid, mucic acid or pamoic acid. Preferably, the di-carboxylic acid is selected from oxalic acid, tartaric acid, succinic acid or fumaric acid, more preferably, oxalic acid.

In one embodiment of either of the first or second aspects of the present invention, the acid is an organic sulfonic acid, such as methanesulfonic, trifluoro-methanesulfonic, ethanesulfonic, 2-hydroxyethanesulphonic, benzenesulfonic, p-toluenesulfonic, naphthalene-2-sulfonic or camphorsulfonic acid. Preferably the organic sulfonic acid is selected from methane sulfonic acid, benzene sulfonic acid or p-toluenesulfonic acid.

Preferably the salt of either of the first or second aspects of the present invention is substantially chemically and regioisomerically pure. For instance, the salt of either of the first or second aspects of the present invention may have a HPLC purity of ≥99.80%. Preferably, the salt has a HPLC purity of ≥99.85% or ≥99.90%, and most preferably the salt has a HPLC purity of ≥99.95%.

As used herein, the percentage HPLC purity is measured by the area normalisation method.

Preferably, the salt of either of the first or second aspects of the present invention is substantially free of the regioisomeric impurity (V) or salts thereof.

A third aspect of the present invention provides a process for the preparation of a salt according to either of the first or second aspects of the present invention, comprising mixing 4-[(1-(1,2,4-triazolyl)methyl]benzonitrile (III) with the acid in a solvent system.

In one embodiment of the third aspect of the present invention, the solvent system comprises a dipolar aprotic solvent such as N,N-dimethylformamide, dimethylsulfoxide, acetonitrile, an ester or a ketone; a polar protic solvent such as an alcohol, a carboxylic acid or an amine; or a mixture thereof. Preferably the solvent system comprises a mixture of a dipolar aprotic solvent and a polar protic solvent.

Where the solvent system comprises a dipolar aprotic solvent, preferably the dipolar aprotic solvent is selected from an ester and a ketone. More preferably the dipolar aprotic solvent is a ketone.

Suitable ketones for use in the solvent system of the third aspect of the present invention include compounds of the formula $R^3COR^4$, wherein $R^3$ and $R^4$ are independently selected from optionally substituted alkyl, alkenyl, alkynyl, aryl, arylalkyl, arylalkenyl, arylalkynyl, alkylaryl, alkenylaryl or alkynylaryl groups, and wherein $R^3$ and $R^4$ together with the carbon atom to which they are attached may form a cyclic hydrocarbyl group which may optionally include one or more heteroatoms N, O or S in its carbon skeleton and which may optionally be substituted. Preferably $R^3$ and $R^4$ are independently selected from optionally substituted alkyl, aryl or arylalkyl groups or together form an optionally substituted alkylene group. More preferably $R^3$ and $R^4$ are optionally substituted $C_{1-8}$ alkyl groups or together form an optionally substituted $C_{1-8}$ alkylene group. More preferably still $R^3$ and $R^4$ are optionally substituted $C_{1-4}$ alkyl groups.

Exemplary ketones for use in the solvent system of the third aspect of the present invention include acetone, methyl ethyl ketone, methyl propyl ketones, diethyl ketone, ethyl propyl ketones, dipropyl ketones, cyclopropanone, cyclohexanone, and mixtures thereof. Preferably the ketone is selected from acetone, methyl ethyl ketone and methyl isopropyl ketone, or mixtures thereof. Most preferably the ketone is acetone.

Where the solvent system comprises a polar protic solvent, preferably the polar protic solvent is an alcohol such as $R^5OH$, wherein $R^5$ is selected from an optionally substituted alkyl, alkenyl, alkynyl, aryl, arylalkyl, arylalkenyl, arylalkynyl, alkylaryl, alkenylaryl or alkynylaryl group. Preferably $R^5$ is an optionally substituted alkyl or arylalkyl group. Mote preferably $R^5$ is an optionally substituted $C_1$ to $C_{20}$ alkyl group, more preferably still $R^5$ is an optionally substituted $C_1$ to $C_{12}$ alkyl group or $C_1$ to $C_6$ alkyl group. Preferably $R^5OH$ is monohydric.

Exemplary alcohols for use in the solvent system of the third aspect of the present invention include methanol, ethanol, 1-propanol, 2-propanol, n-butanol, iso-butanol, sec-butanol, tert-butanol, n-pentanol, cyclopentanol, cyclohexanol, and mixtures thereof. Preferably the alcohol is selected from methanol, ethanol, 1-propanol, 2-propanol, 1-butanol and tertiary butanol, or mixtures thereof. Most preferably the alcohol is methanol.

In a preferred embodiment of the third aspect of the present invention, the solvent system comprises one or more solvents selected from straight chain or branched aliphatic ketones and aliphatic $C_1$ to $C_4$ alcohols, or mixtures thereof. Preferably the ketone is selected from acetone, methyl ethyl ketone and methyl isopropyl ketone, or mixtures thereof. Preferably, the alcohol is selected from methanol, ethanol, 1-propanol, 2-propanol, 1-butanol and tertiary butanol, or mixtures thereof.

As used herein, the term "aliphatic" refers to acyclic or cyclic, saturated or unsaturated carbon containing compounds, excluding aromatic compounds.

In one embodiment of the third aspect of the present invention, where the solvent system comprises a dipolar aprotic solvent and a polar protic solvent, for example acetone and an alcohol, the ratio of dipolar aprotic solvent to polar protic solvent in the solvent system is from 95:5 to 5:95 by volume. Preferably the ratio is from 80:20 to 20:80 by volume, more preferably from 60:40 to 40:60 by volume. Most preferably the ratio is about 50:50 by volume.

Most preferably, the solvent system comprises acetone and methanol, and preferably the ratio of acetone:methanol in the solvent mixture is 95:5, more preferably 80:20, more preferably 60:40 and most preferably 50:50 by volume.

In one embodiment of the third aspect of the present invention, from 1 to 10 volumes of solvent are used in the solvent system in total, i.e. for every 1 g of 4-[(1-(1,2,4-triazolyl) methyl]benzonitrile (III), from 1 to 10 ml of solvent are used. Preferably from 2 to 6 volumes of solvent are used. Most preferably about 4 volumes of the solvent are used.

Preferably the acid is reacted with 4-[(1-(1,2,4-triazolyl) methyl]benzonitrile (III) at a temperature of 10 to 60° C., more preferably at 20 to 40° C. and most preferably at 25 to 30° C.

Typically, from 1 to 10 equivalents of the acid may be used, relative to the 4-[(1-(1,2,4-triazolyl)methyl]benzonitrile (III). Preferably from 1 to 5 equivalents of the acid are used, more preferably from 1 to 1.5 equivalents of the acid are used, and most preferably about 1.05 equivalents of the acid are used.

A fourth aspect of the present invention provides a process for the preparation of 4-[(1-(1,2,4-triazolyl)methyl]benzonitrile (III), comprising the reaction of 4-bromo-methylbenzonitrile with 1,2,4-triazole in the presence of a base and a catalytic quantity of iodide ion in a solvent system.

In one embodiment of the fourth aspect of the present invention, the solvent system comprises a ketone and/or an alcohol. Preferably, the solvent system comprises one or more solvents selected from straight chain or branched aliphatic ketones and aliphatic $C_1$ to $C_4$ alcohols, or mixtures thereof.

A fifth aspect of the present invention provides a process for the preparation of 4-[(1-(1,2,4-triazolyl)methyl]benzonitrile (III), comprising the reaction of 4-bromo-methylbenzonitrile with 1,2,4-triazole in a solvent system comprising a ketone and an alcohol. Optionally the reaction is performed in the presence of a base and/or a catalytic quantity of iodide ion.

Suitable ketones for use in the solvent systems of the fourth and fifth aspects of the present invention include compounds of the formula $R^6COR^7$, wherein $R^6$ and $R^7$ are independently selected from optionally substituted alkyl, alkenyl, alkynyl, aryl, arylalkyl, arylalkenyl, arylalkynyl, alkylaryl, alkenylaryl or alkynylaryl groups, or wherein $R^6$ and $R^7$ together with the carbon atom to which they are attached may form a cyclic hydrocarbyl group which may optionally include one or more heteroatoms N, O or S in its carbon skeleton and which may optionally be substituted. Preferably $R^6$ and $R^7$ are independently selected from optionally substituted alkyl, aryl or arylalkyl groups or together form an optionally substituted alkylene group. More preferably $R^6$ and $R^7$ are optionally substituted $C_{1-8}$ alkyl groups or together form an optionally substituted $C_{1-8}$ alkylene group. More preferably still $R^6$ and $R^7$ are optionally substituted $C_{1-4}$ alkyl groups.

Exemplary ketones for use in the solvent systems of the fourth and fifth aspects of the present invention include acetone, methyl ethyl ketone, methyl propyl ketones, diethyl ketone, ethyl propyl ketones, dipropyl ketones, cyclopropanone, cyclohexanone, and mixtures thereof. Preferably, the ketone is selected from acetone, methyl ethyl ketone and methyl isopropyl ketone, or mixtures thereof. Most preferably the ketone is acetone.

Suitable alcohols for use in the solvent systems of the fourth and fifth aspects of the present invention include compounds of the formula $R^8OH$, wherein $R^8$ is selected from an optionally substituted alkyl, alkenyl, alkynyl, aryl, arylalkyl, arylalkenyl, arylalkynyl, alkylaryl, alkenylaryl or alkynylaryl group. Preferably $R^8$ is an optionally substituted alkyl or arylalkyl group. More preferably $R^8$ is an optionally substituted $C_1$ to $C_{20}$ alkyl group, more preferably still $R^8$ is an optionally substituted $C_1$ to $C_{12}$ alkyl group or $C_1$ to $C_6$ alkyl group. Preferably $R^8OH$ is monohydric.

Exemplary alcohols for use in the solvent systems of the fourth and fifth aspects of the present invention include methanol, ethanol, 1-propanol, 2-propanol, n-butanol, iso-butanol, sec-butanol, tert-butanol, n-pentanol, cyclopentanol, cyclohexanol, and mixtures thereof. Preferably, the alcohol is selected from methanol, ethanol, 1-propanol, 2-propanol, 1-butanol and tertiary butanol, or mixtures thereof. Most preferably the alcohol is methanol.

In one embodiment of either of the fourth or fifth aspects of the present invention, where the solvent system comprises a ketone and an alcohol, the ratio of ketones to alcohols in the solvent system is from 95:5 to 5:95 by volume. Preferably the ratio is from 80:20 to 20:80 by volume, more preferably from 60:40 to 40:60 by volume. Most preferably the ratio is about 50:50 by volume.

Most preferably, the solvent system comprises acetone and methanol. Preferably, the ratio of acetone:methanol in the solvent system is 95:5, more preferably 80:20, more preferably 60:40 and most preferably 50:50 by volume.

In one embodiment of either of the fourth or fifth aspects of the present invention, from 1 to 100 volumes of solvent are used in the solvent system, i.e. for every 1 g of 4-bromomethylbenzonitrile starting material, from 1 to 100 ml of solvent are used. Preferably from 2 to 25 volumes of solvent are used, more preferably from 5 to 15 volumes of solvent are used. Most preferably about 10 volumes of solvent are used.

Preferably the 4-bromomethylbenzonitrile is reacted with 1,2,4-triazole at a temperature of 20 to 100° C., more preferably at 20 to 60° C., more preferably at 20 to 40° C. and most preferably at 25 to 30° C.

Typically, the 4-bromomethylbenzonitrile is reacted with the 1,2,4-triazole over a period of from 30 minutes to 48 hours. Preferably, the 4-bromomethylbenzonitrile is reacted with the 1,2,4-triazole over a period of from 1 to 12 hours, more preferably over a period of from 2 to 6 hours. Most preferably the 4-bromomethyl-benzonitrile is reacted with the 1,2,4-triazole over a period of from 3 to 5 hours.

Typically, from 0.5 to 10 equivalents of 1,2,4-triazole may be used, relative to the 4-bromomethylbenzonitrile. Preferably from 0.75 to 5 equivalents of 1,2,4-triazole are used, and most preferably about 1 equivalent of 1,2,4-triazole is used.

In a preferred embodiment of either of the fourth or fifth aspects of the present invention, the 1,2,4-triazole is added to the reaction mixture as a free base, i.e. not in salt form.

In one embodiment of either of the fourth or fifth aspects of the present invention, the base is a carbonate or a bicarbonate. Preferably the base is a metal or ammonium carbonate or bicarbonate, such as sodium carbonate, sodium bicarbonate, potassium carbonate, potassium bicarbonate, ammonium carbonate or ammonium bicarbonate. Mote preferably, the base is a metal carbonate, most preferably potassium carbonate or sodium carbonate.

Typically, from 0.5 to 10 equivalents of base may be used, relative to the 4-bromo-methylbenzonitrile. Preferably from 0.75 to 5 equivalents of base are used, and most preferably about 1 equivalent of base is used.

Preferably, the iodide ion is present as potassium iodide or sodium iodide.

Typically, from 0.01 to 1 equivalents of iodide ion may be used, relative to the 4-bromomethylbenzonitrile. Preferably from 0.05 to 0.5 equivalents of iodide ion are used, and most preferably about 0.1 equivalents of iodide ion are used.

On completion of the reaction, the reaction mixture may optionally be quenched, for example by the addition of water and/or an acid such as acetic acid. Preferably the pH of the reaction mixture is adjusted to between 5 and 8. More preferably the pH of the reaction mixture is adjusted to between 6 and 7.

In one embodiment of either of the fourth or fifth aspects of the present invention, the 4-[(1-(1,2,4-triazolyl)methyl]benzonitrile (III) formed is converted into a salt. Preferably, the 4-[(1-(1,2,4-triazolyl)methyl]benzonitrile (III) formed is converted into a salt according to a process of the third aspect of the present invention.

A sixth aspect of the present invention provides a process for the preparation of 4-[(1-(1,2,4-triazolyl)methyl]benzonitrile (III), comprising the purification of a salt according to either of the first or second aspects of the present invention, or of a salt prepared by a process according to any of the third to fifth aspects of the present invention, and the subsequent liberation of 4-[(1-(1,2,4-triazolyl)methyl]-benzonitrile (III) from the purified salt.

In one embodiment of the sixth aspect of the present invention, the salt is purified by crystallisation from a solvent system. Optionally, the solvent system may comprise a dipolar aprotic solvent such as N,N-dimethylformamide, dimethylsulfoxide, acetonitrile, an ester or a ketone; a polar protic solvent such as an alcohol, a carboxylic acid or an amine; or a mixture thereof. Preferably the solvent system comprises a mixture of a dipolar aprotic solvent and a polar protic solvent.

Where the solvent system comprises a dipolar aprotic solvent, preferably the dipolar aprotic solvent is selected from an ester and a ketone. More preferably the dipolar aprotic solvent is a ketone.

Suitable ketones for use in the solvent system of the sixth aspect of the present invention include compounds of the formula $R^9COR^{10}$, wherein $R^9$ and $R^{10}$ are independently selected from optionally substituted alkyl, alkenyl, alkynyl, aryl, arylalkyl, arylalkenyl, arylalkynyl, alkylaryl, alkenylaryl or alkynylaryl groups, and wherein $R^9$ and $R^{10}$ together with the carbon atom to which they are attached may form a cyclic hydrocarbyl group which may optionally include one or more heteroatoms N, O or S in its carbon skeleton and which may optionally be substituted. Preferably $R^9$ and $R^{10}$ are independently selected from optionally substituted alkyl, aryl or arylalkyl groups or together form an optionally substituted alkylene group. More preferably $R^9$ and $R^{10}$ are optionally substituted $C_{1-8}$ alkyl groups or together form an optionally substituted $C_{1-8}$ alkylene group. More preferably still $R^9$ and $R^{10}$ are optionally substituted $C_{1-4}$ alkyl groups.

Exemplary ketones for use in the solvent system of the sixth aspect of the present invention include acetone, methyl ethyl ketone, methyl propyl ketones, diethyl ketone, ethyl propyl ketones, dipropyl ketones, cyclopropanone, cyclohexanone, and mixtures thereof. Preferably the ketone is selected from acetone, methyl ethyl ketone and methyl isopropyl ketone, or mixtures thereof. Most preferably the ketone is acetone.

Where the solvent system comprises a polar protic solvent, preferably the polar protic solvent is an alcohol such as $R^{11}OH$, wherein $R^{11}$ is selected from an optionally substituted alkyl, alkenyl, alkynyl, aryl, arylalkyl, arylalkenyl, arylalkynyl, alkylaryl, alkenylaryl or alkynylaryl group. Preferably $R^{11}$ is an optionally substituted alkyl or arylalkyl group. More preferably $R^{11}$ is an optionally substituted $C_1$ to $C_{20}$ alkyl group, more preferably still $R^{11}$ is an optionally substituted $C_1$ to $C_{12}$ alkyl group or $C_1$ to $C_6$ alkyl group. Preferably $R^{11}OH$ is monohydric.

Exemplary alcohols for use in the solvent system of the sixth aspect of the present invention include methanol, ethanol, 1-propanol, 2-propanol, n-butanol, iso-butanol, sec-butanol, tert-butanol, n-pentanol, cyclopentanol, cyclohexanol, and mixtures thereof. Preferably the alcohol is selected from methanol, ethanol, 1-propanol, 2-propanol, 1-butanol and tertiary butanol, or mixtures thereof. Most preferably the alcohol is methanol.

In a preferred embodiment of the sixth aspect of the present invention, the solvent system comprises one or more solvents selected from straight chain or branched aliphatic ketones and aliphatic $C_1$ to $C_4$ alcohols, or mixtures thereof. Preferably, the ketone is selected from acetone, methyl ethyl ketone and methyl isopropyl ketone, or mixtures thereof. Preferably, the alcohol is selected from methanol, ethanol, 1-propanol, 2-propanol, 1-butanol and tertiary butanol, or mixtures thereof.

In one embodiment of the sixth aspect of the present invention, where the solvent system comprises a dipolar aprotic solvent and a polar protic solvent, for example acetone and an alcohol, the ratio of dipolar aprotic solvent to polar protic solvent in the solvent system is from 95:5 to 5:95 by volume. Preferably the ratio is from 80:20 to 20:80 by volume, more preferably from 60:40 to 40:60 by volume. Most preferably the ratio is about 50:50 by volume.

Most preferably, the solvent system comprises acetone and methanol. Preferably, the ratio of acetone:methanol in the solvent system is 95:5, more preferably 80:20, more preferably 60:40 and most preferably 50:50 by volume.

In one embodiment of the sixth aspect of the present invention, from 1 to 10 volumes of solvent are used in the solvent system in total, i.e. for every 1 g of 4-[(1-(1,2,4-triazolyl)methyl]benzonitrile salt, from 1 to 10 ml of solvent are used. Preferably from 2 to 6 volumes of solvent are used. Most preferably about 3 volumes of solvent are used.

Preferably the salt is purified in the solvent system at a temperature of 10 to 60° C., more preferably at 20 to 40° C. and most preferably at 25 to 30° C.

In one embodiment of the sixth aspect of the present invention, the 4-[(1-(1,2,4-triazolyl)methyl]benzonitrile (III) is liberated from the purified salt by treatment with a base. Preferably the 4-[(1-(1,2,4-triazolyl)methyl]benzonitrile (III) is liberated from the purified salt by treatment with an aqueous base.

Typically, from 1 to 10 volumes of water are used in the aqueous base, i.e. for every 1 g of 4-[(1-(1,2,4-triazolyl)methyl]benzonitrile salt, from 1 to 10 ml of water are used. Preferably from 2 to 6 volumes of water are used. Most preferably about 3 volumes of water are used.

The base may be an organic base such as an amine or an alkoxide, or an inorganic base such as ammonia, a hydroxide, a carbonate or a bicarbonate. Preferably the base is an alkoxide or a hydroxide. More preferably the base is a metal or ammonium hydroxide, such as lithium hydroxide, sodium hydroxide, potassium hydroxide, calcium hydroxide or ammonium hydroxide. Most preferably the base is sodium hydroxide.

Typically, the 4-[(1-(1,2,4-triazolyl)methyl]benzonitrile (III) is liberated from the purified salt by adjusting the pH of a solution or suspension of the salt to ≥7. Preferably, the pH is adjusted to from 7 to 10, more preferably to from 7 to 8.

Preferably the 4-[(1-(1,2,4-triazolyl)methyl]benzonitrile (III) is liberated at a temperature of −20 to 40° C., more preferably at 0 to 30° C. and most preferably at 10 to 15° C.

Optionally, the liberated 4-[(1-(1,2,4-triazolyl)methyl]benzonitrile (III) is further purified by dissolving it in an organic solvent, and removing insoluble impurities such as metal or ammonium salts of the acid, e.g. sodium oxalate. Typically, from 1 to 50 volumes of organic solvent are used, i.e. for every 1 g of 4-[(1-(1,2,4-triazolyl)methyl]benzonitrile (III), from 1 to 50 ml of organic solvent are used. Preferably from 5 to 20 volumes of solvent are used. Most preferably about 10 volumes of organic solvent are used.

Preferably the organic solvent is selected from a non-polar solvent or a dipolar aprotic solvent, or a mixture thereof. More preferably the organic solvent is selected from a non-polar solvent. Exemplary non-polar solvents include alkanes and cycloalkanes such as n-hexane, cyclohexane or n-heptane, aromatic hydrocarbons such as toluene or benzene, alkyl ethers and cycloalkyl ethers such as diethyl ether, tert-butyl methyl ether, tetrahydrofuran (THF) or 1,4-dioxane, and chlorohydrocarbons such as chloroform or dichloromethane (DCM). Preferably the non-polar solvent is a chlorohydrocarbon, most preferably dichloromethane.

Alternatively or in addition, the liberated 4-[(1-(1,2,4-triazolyl)methyl]benzonitrile (III) may be further purified by crystallisation from a solvent system. Preferably the solvent system comprises a non-polar solvent such as an alkane or a cycloalkane, e.g. n-hexane, cyclohexane or n-heptane; an aromatic hydrocarbon, e.g. toluene or benzene; an alkyl ether or a cycloalkyl ether, e.g. diethyl ether, tert-butyl methyl ether, tetrahydrofuran (THF) or 1,4-dioxane; a chlorohydrocarbon, e.g. chloroform or dichloromethane (DCM); or a mixture thereof. More preferably the solvent system comprises an alkane or a cycloalkane. Most preferably the solvent system comprises n-heptane.

A seventh aspect of the present invention provides 4-[(1-(1,2,4-triazolyl)methyl]benzonitrile (III) or a salt thereof, when prepared by a process according to any other aspect of the present invention.

In one embodiment of the seventh aspect of the present invention, the 4-[(1-(1,2,4-triazolyl)methyl]benzonitrile (III), or the salt thereof, has a HPLC purity of equal to or more than 99.8%.

An eighth aspect of the present invention provides 4-[(1-(1,2,4-triazolyl)methyl]benzonitrile (III) or a salt thereof, with a HPLC purity of equal to or more than 99.8%.

In one embodiment of either of the seventh or eighth aspects of the present invention, 4-[(1-(1,2,4-triazolyl)methyl]benzonitrile (III) or a salt thereof with a HPLC purity of ≥99.85% is provided. More preferably 4-[(1-(1,2,4-triazolyl)methyl]benzonitrile (III) or a salt thereof with a HPLC purity of ≥99.90% is provided, and most preferably 4-[(1-(1,2,4-triazolyl)methyl]benzonitrile (III) or a salt thereof with a HPLC purity of ≥99.95% is provided.

In another embodiment of either of the seventh or eighth aspects of the present invention, the 4-[(1-(1,2,4-triazolyl)methyl]benzonitrile (III) or the salt thereof is substantially free of the regioisomeric impurity (V) or salts thereof.

A ninth aspect of the present invention provides 4-[(1-(1,2,4-triazolyl)methyl]-benzonitrile (III) or the salt thereof, substantially free of the regioisomeric impurity (V) or salts thereof.

A tenth aspect of the present invention provides anhydrous crystalline 4-[(1-(1,2,4-triazolyl)methyl]benzonitrile (III), preferably having an X-ray powder diffraction pattern comprising at least 3 characteristic peaks at about 4.91, 7.60, 8.70, 11.80, 12.65, 15.80, 16.74, 17.31, 18.47, 20.13, 21.22, 21.73, 22.88, 23.26, 24.10, 26.01, 28.25 and 29.40 degrees 2θ±0.2, more preferably at least 7 characteristic peaks at about 4.91, 7.60, 8.70, 11.80, 12.65, 15.80, 16.74, 17.31, 18.47, 20.13, 21.22, 21.73, 22.88, 23.26, 24.10, 26.01, 28.25 and 29.40 degrees 2θ±0.2. Most preferably the anhydrous crystalline 4-[(1-(1,2,4-triazolyl)methyl]benzonitrile (III) has an X-ray powder diffraction pattern comprising characteristic peaks at each of about 4.91, 7.60, 8.70, 11.80, 12.65, 15.80, 16.74, 17.31, 18.47, 20.13, 21.22, 21.73, 22.88, 23.26, 24.10, 26.01, 28.25 and 29.40 degrees 2θ±0.2.

Figure 3:
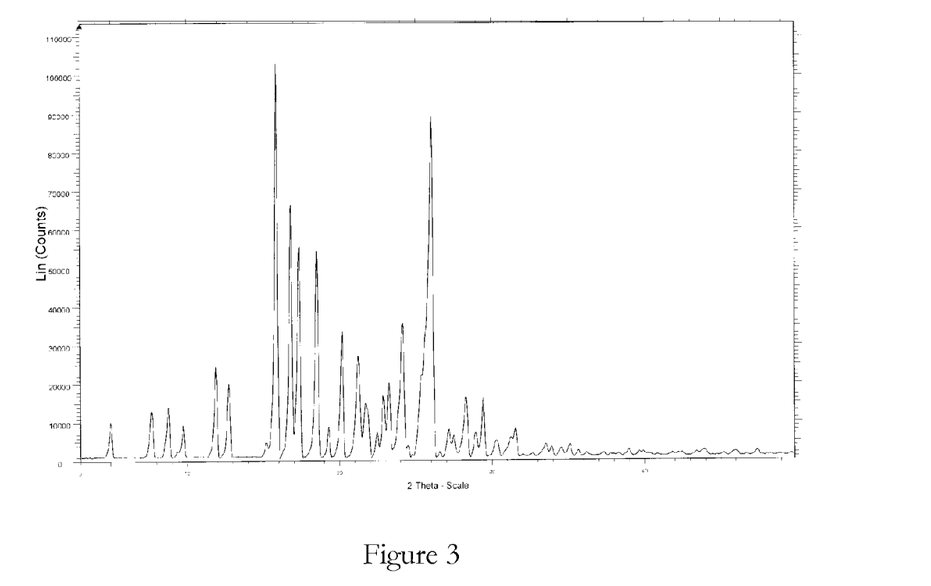
FIG. 3: XRPD of the anhydrous crystalline intermediate 4-[(1-(1,2,4-triazolyl)methyl]benzonitrile (III) according to the invention.
Figure 4:
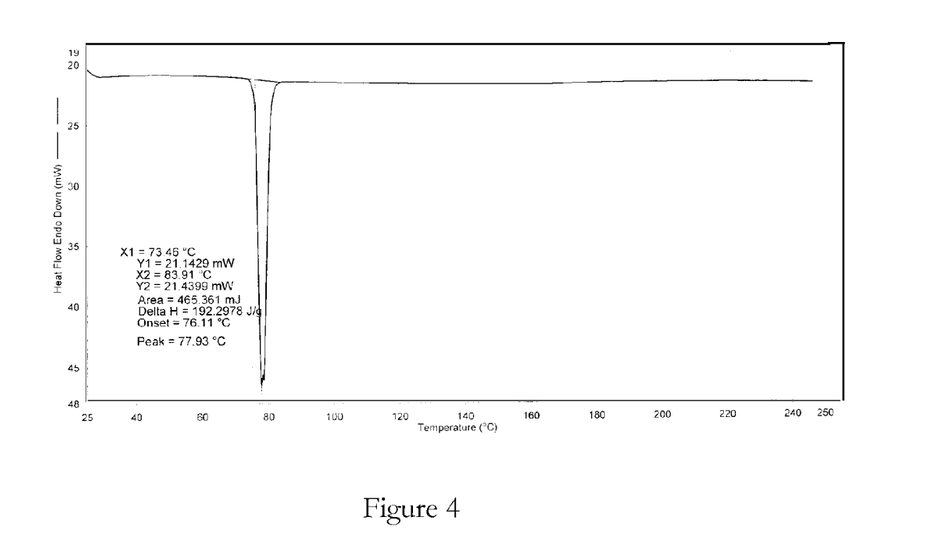
FIG. 4: Differential Scanning Calorimetry of the anhydrous crystalline intermediate 4-[(1-(1,2,4-triazolyl)methyl] benzonitrile (III) according to the invention.
Figure 5:
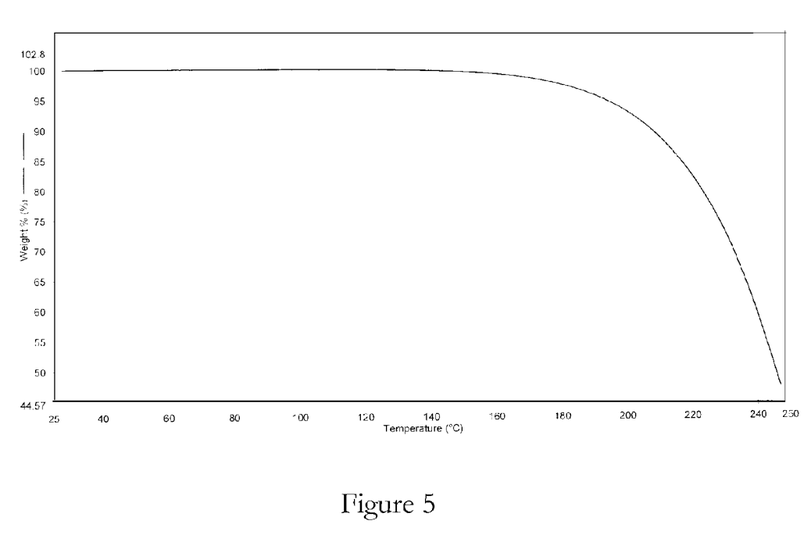
FIG. 5: Thermogravimetric analysis of the anhydrous crystalline intermediate 4-[(1-(1,2,4-triazolyl)methyl]benzonitrile (III) according to the invention.

In one embodiment of the tenth aspect of the present invention, the anhydrous crystalline 4-[(1-(1,2,4-triazolyl)methyl]benzonitrile (III) has an X-ray powder diffraction pattern substantially as shown in FIG. 3, and/or a differential scanning calorimetry (DSC) trace substantially as shown in FIG. 4, and/or a thermogravimetric analysis (TGA) trace substantially as shown in FIG. 5.

Preferably the crystalline anhydrous form has a single endothermic peak at 77 to 79° C. on differential scanning calorimetry (DSC) analysis.

Preferably, the anhydrous crystalline 4-[(1-(1,2,4-triazolyl)methyl]benzonitrile (III) is substantially free of the regioisomeric impurity (V) or salts thereof.

In one embodiment of the tenth aspect of the present invention, the anhydrous crystalline 4-[(1-(1,2,4-triazolyl)methyl]benzonitrile (III) has a HPLC purity of ≥99.80%. Preferably the anhydrous crystalline 4-[(1-(1,2,4-triazolyl)methyl]-benzonitrile (III) has a HPLC purity of ≥99.85%, more preferably ≥99.90%. Most preferably the anhydrous crystalline 4-[(1-(1,2,4-triazolyl)methyl]-benzonitrile (III) has a HPLC purity of ≥99.95%.

An eleventh aspect of the present invention provides a process for the preparation of Letrozole (I) or a salt such as a pharmaceutically acceptable salt thereof, wherein the process uses a salt according to either of the first or second aspects of the present invention, 4-[(1-(1,2,4-triazolyl)methyl]benzonitrile (III) or a salt thereof according to any of the seventh to ninth aspects of the present invention, or anhydrous crystalline 4-[(1-(1,2,4-triazolyl)methyl]benzonitrile (III) according to the tenth aspect of the present invention.

Optionally, the salt according to either of the first or second aspects of the present invention, the 4-[(1-(1,2,4-triazolyl)methyl]benzonitrile (III) or salt thereof according to any of the seventh to ninth aspects of the present invention, or the anhydrous crystalline 4-[(1-(1,2,4-triazolyl)methyl]benzonitrile (III) according to the tenth aspect of the present invention is used as an intermediate.

Similarly, in one embodiment of any of the third to sixth aspects of the present invention, the 4-[(1-(1,2,4-triazolyl)methyl]benzonitrile (III) or the salt thereof which is prepared may be further converted into Letrozole (I) or a salt such as a pharmaceutically acceptable salt thereof.

In one embodiment of any of the third to sixth or eleventh aspects of the present invention, the 4-[(1-(1,2,4-triazolyl)methyl]benzonitrile (III) or the salt thereof is further converted into Letrozole (I) or a salt such as a pharmaceutically acceptable salt thereof by reaction with 4-fluorobenzonitrile (IV), preferably at a temperature of −20° C. to 0° C., more preferably at a temperature of −20° C. to −10° C. and most preferably at a temperature of −20° C. to −15° C.

In one embodiment, from 0.5 to 10 equivalents of 4-fluorobenzonitrile (IV) may be used, relative to the 4-[(1-(1,2,4-triazolyl)methyl]benzonitrile (III). Preferably from 0.75 to 5 equivalents of 4-fluorobenzonitrile (IV) are used, and most preferably about 1 equivalent of 4-fluorobenzonitrile (IV) is used.

In another embodiment, the reaction with 4-fluorobenzonitrile (IV) occurs in the presence of a base. Preferably the base is non-nucleophilic. Suitable bases include tertiary amines such as triethylamine, diisopropylethylamine and 1,8-diazabicyclo-undec-7-ene (DBU), branched alkoxides such as tert-butoxides, hydrides such as NaH, and organometallic bases such as lithium diisopropylamide. Preferably the base is a branched alkoxide, more preferably a metal tert-butoxide and most preferably potassium tert-butoxide.

Typically, from 0.5 to 10 equivalents of base may be used, relative to the 4-[(1-(1,2,4-triazolyl)methyl]benzonitrile (III). Preferably from 1 to 5 equivalents of base are used, and most preferably about 3 equivalents of base are used.

Optionally, the base is combined with the 4-[(1-(1,2,4-triazolyl)methyl]benzonitrile (III) prior to the addition of the 4-fluorobenzonitrile (IV).

In one embodiment of any of the third to sixth or eleventh aspects of the present invention, the reaction of the 4-[(1-(1,2,4-triazolyl)methyl]benzonitrile (III) or the salt thereof with the 4-fluorobenzonitrile (IV) occurs in a dipolar aprotic solvent such as N,N-dimethylformamide, dimethylsulfoxide, acetonitrile, an ester or a ketone. Preferably the reaction occurs in N,N-dimethylformamide, dimethylsulfoxide or acetonitrile. Most preferably the reaction occurs in N,N-dimethylformamide.

Typically, the reaction of the 4-[(1-(1,2,4-triazolyl)methyl] benzonitrile (III) or the salt thereof with 4-fluorobenzonitrile (IV) is performed in 1 to 50 volumes of solvent, i.e. for every 1 g of 4-[(1-(1,2,4-triazolyl)methyl]benzonitrile (III), from 1 to 50 ml of solvent are used. Preferably from 2 to 20 volumes of solvent are used. More preferably from 5 to 10 volumes of solvent are used. Most preferably about 6.5 volumes of solvent are used.

On completion of the reaction, the reaction mixture may optionally be quenched, for example by the addition of an acid such as acetic acid. Preferably the reaction mixture is adjusted to a pH of from 4 to 7. More preferably the reaction mixture is adjusted to a pH of from 5 to 6.

Optionally, the reaction mixture is purified by dilution with an organic solvent, followed by the removal of insoluble impurities such as salts of the quenching acid, e.g. potassium acetate. Preferably the organic solvent is selected from a non-polar solvent or a dipolar aprotic solvent, or a mixture thereof. More preferably the organic solvent is selected from a non-polar solvent. Exemplary non-polar solvents include alkanes and cycloalkanes such as n-hexane, cyclohexane or n-heptane, aromatic hydrocarbons such as toluene or benzene, alkyl ethers and cycloalkyl ethers such as diethyl ether, tert-butyl methyl ether (TBME), tetrahydrofuran (THF) or 1,4-dioxane, and chlorohydrocarbons such as chloroform or dichloromethane (DCM). Preferably the non-polar solvent is a chlorohydrocarbon, most preferably dichloromethane.

Optionally, in any aspect of the present invention in which Letrozole (I) is prepared, the 4-[(1-(1,2,4-triazolyl)methyl] benzonitrile (III) or the salt thereof is not isolated and is used in situ.

In any aspect of the present invention in which Letrozole (I) is prepared, the Letrozole (I) may be further purified, for instance by one or more crystallisations.

A twelfth aspect of the present invention provides a process for the purification of Letrozole (I) or a pharmaceutically acceptable salt thereof, comprising the crystallisation of Letrozole (I) from a solvent system comprising methanol and n-heptane. Optionally, the Letrozole may be prepared by a process according to any other aspect of the present invention.

In one embodiment of the twelfth aspect of the present invention, the ratio of methanol to n-heptane in the solvent system is from 50:50 to 10:90 by volume. Preferably the ratio of methanol to n-heptane in the solvent system is from 40:60 to 20:80 by volume. Most preferably the ratio of methanol to n-heptane in the solvent system is about 20:50 by volume.

A thirteenth aspect of the present invention provides a process for the purification of Letrozole (I) or a pharmaceutically acceptable salt thereof, comprising the crystallisation of Letrozole (I) from a solvent system comprising:
(a) an alkyl formate, alkyl acetate, alkyl propionate, alkyl butyrate or alkyl isobutyrate; and
(b) a $C_5$ to $C_{12}$ ether.

Optionally, the Letrozole may be prepared by a process according to any other aspect of the present invention.

In one embodiment of the thirteenth aspect of the present invention, the ratio of (a) to (b) in the solvent system is from 60:40 to 90:10 by volume. Preferably the ratio of (a) to (b) in the solvent system is from 70:30 to 80:20 by volume. Most preferably the ratio of (a) to (b) in the solvent system is about 75:25 by volume.

In another embodiment of the thirteenth aspect of the present invention, the alkyl group of the alkyl formate, alkyl acetate, alkyl propionate, alkyl butyrate or alkyl isobutyrate is a $C_1$ to $C_6$ alkyl group. Preferably the alkyl group is a $C_1$ to $C_4$ alkyl group such as methyl, ethyl, n-propyl, i-propyl, n-butyl, i-butyl or t-butyl. Most preferably the alkyl group is ethyl.

In yet another embodiment of the thirteenth aspect of the present invention, the solvent system comprises:
(a) an alkyl acetate; and
(b) a $C_5$ to $C_{12}$ ether.

As used herein, a $C_5$ to $C_{12}$ ether is defined as an ether containing from 5 to 12 carbon atoms. Suitable ethers for use in the solvent system of the thirteenth aspect of the present invention include compounds of the formula $R^{12}OR^{13}$, wherein $R^{12}$ and $R^{13}$ are independently selected from optionally substituted alkyl, alkenyl, alkynyl, aryl, arylalkyl, arylalkenyl, arylalkynyl, alkylaryl, alkenylaryl or alkynylaryl groups, and wherein $R^{12}$ and $R^{13}$ together with the carbon atom to which they are attached may form a cyclic hydrocarbyl group which may optionally include one or more heteroatoms N, O or S in its carbon skeleton and which may optionally be substituted. Preferably $R^{12}$ and $R^{13}$ are independently selected from optionally substituted alkyl, aryl or arylalkyl groups or together form an optionally substituted alkylene group. More preferably $R^{12}$ and $R^{13}$ are optionally substituted $C_{1-8}$ alkyl groups or together form an optionally substituted $C_{1-8}$ alkylene group. More preferably still $R^{12}$ and $R^{13}$ are optionally substituted $C_{1-4}$ alkyl groups.

Preferably, the $C_5$ to $C_{12}$ ether used in the thirteenth aspect of the present invention is a $C_5$ to $C_8$ ether such as tert-butyl methyl ether (TBME).

Most preferably, the solvent system of the thirteenth aspect of the present invention comprises ethyl acetate and tert-butyl methyl ether (TBME).

In one embodiment of either of the twelfth or thirteenth aspects of the present invention, the crystallisation is performed at a temperature of from −20 to 50° C. Preferably, the crystallisation is performed at a temperature of from 0 to 30° C., more preferably from 5 to 20° C., and most preferably from 10 to 15° C.

A fourteenth aspect of the present invention provides Letrozole, or a salt thereof such as a pharmaceutically acceptable salt, when prepared or purified by a process according to any of the third to sixth or eleventh to thirteenth aspects of the present invention.

Preferably the Letrozole or the salt thereof according to the fourteenth aspect of the present invention has a HPLC purity equal to or more than 99.9%.

A fifteenth aspect of the present invention provides Letrozole, or a salt thereof such as a pharmaceutically acceptable salt, with a HPLC purity equal to or more than 99.9%.

In one embodiment of either of the fourteenth or fifteenth aspects of the present invention, Letrozole, or a salt thereof, with a HPLC purity of ≥99.95% is provided. Preferably Letrozole, or a salt thereof, with a HPLC purity of ≥99.98% is provided.

In another embodiment of either of the fourteenth or fifteenth aspects of the present invention, the Letrozole or the salt thereof is substantially free of the regioisomeric impurity (II) or salts thereof.

A sixteenth aspect of the present invention provides Letrozole or a salt thereof such as a pharmaceutically acceptable salt, substantially free of the regioisomeric impurity (II) or salts thereof.

A seventeenth aspect of the present invention provides Letrozole or a pharmaceutically acceptable salt thereof according to any of the fourteenth to sixteenth aspects of the present invention, for use in medicine.

An eighteenth aspect of the present invention provides a pharmaceutical composition comprising Letrozole, or a pharmaceutically acceptable salt thereof, according to any of the fourteenth to seventeenth aspects of the present invention. Preferably the pharmaceutical composition further comprises one or more pharmaceutically acceptable excipients.

A nineteenth aspect of the present invention provides Letrozole, or a pharmaceutically acceptable salt thereof, according to any of the fourteenth to seventeenth aspects of the present invention, or a pharmaceutical composition according to the eighteenth aspect of the present invention, for use as an aromatase inhibitor.

A twentieth aspect of the present invention provides Letrozole, or a pharmaceutically acceptable salt thereof, according to any of the fourteenth to seventeenth aspects of the present invention, or a pharmaceutical composition according to the eighteenth aspect of the present invention, for use in the treatment or prevention of cancer. Preferably the cancer is breast cancer.

A twenty-first aspect of the present invention provides the use of Letrozole, or a pharmaceutically acceptable salt thereof, according to any of the fourteenth to seventeenth aspects of the present invention, or of a pharmaceutical composition according to the eighteenth aspect present invention, in the manufacture of a medicament for the treatment of cancer. Preferably the cancer is breast cancer.

A twenty-second aspect of the present invention provides a method of treating or preventing cancer, comprising administering a therapeutically or prophylactically effective amount of Letrozole, or a pharmaceutically acceptable salt thereof, according to any of the fourteenth to seventeenth aspects of the present invention, or of a pharmaceutical composition according to the eighteenth aspect present invention, to a patient in need thereof. Preferably the cancer is breast cancer.

In a preferred embodiment of the twenty-second aspect of the present invention, the patient is a mammal. More preferably the patient is a human.

The term "Letrozole" as used herein throughout the description and claims means Letrozole and/or any salt, solvate such as a hydrate, or polymorph thereof, unless otherwise specified.

Unless otherwise specified, the compounds of the present invention can be used both in their free base form and their acid addition salt form. For the purposes of this invention, a "salt" of a compound of the present invention may be an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulfuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulfonic acids (for example, methanesulfonic, trifluoromethanesulfonic, ethanesulfonic, 2-hydroxyethanesulphonic, benzenesulfonic, toluene-p-sulfonic, naphthalene-2-sulfonic or camphorsulfonic acid) or amino acids (for example, ornithinic, glutamic or aspartic acid). The acid addition salt may be a mono- or di-acid addition salt.

Unless otherwise specified, a preferred salt is a hydrohalogenic, sulfuric, phosphoric or organic acid addition salt.

In addition to pharmaceutically acceptable acid addition salts, other acid addition salts are included in the present invention, since they have potential to serve as intermediates in the purification or preparation of other, for example, pharmaceutically acceptable, acid addition salts, or are useful for identification, characterisation or purification of the free base.

For the purposes of the present invention, the Letrozole (I) and 4-[(1-(1,2,4-triazolyl)methyl]-benzonitrile (III) and their salts are "substantially free" of chemical or regioisomeric impurities, if they comprise less than 0.3% impurity by HPLC, preferably less than 0.2%, preferably less than 0.1% and most preferably less than 0.05%.

For the avoidance of doubt, insofar as is practicable any embodiment of a given aspect of the present invention may occur in combination with any other embodiment of the same aspect of the present invention. In addition, insofar as is practicable it is to be understood that any preferred or optional embodiment of any aspect of the present invention should also be considered as a preferred or optional embodiment of any other aspect of the present invention.

Equipment detail and conditions used for the testing:
XRPD: Recorded on Bruker D8 Advance diffractometer using a CuKα1 source.
DSC: Recoded on Perkin Elmer Pyris 6 over a range of 25° C. to 250° C. at a rate of 10° C./min
TGA: Thermo Gravimetric analysis (TGA) was carried out on Perkin Elmer Pyris 1 and recorded over a range of 25° C. to 250° C. at a rate 10° C. per minute. No weight loss was observed.
HPLC: System: Waters E-2695
Detector: W 2489; at wavelength 230 nm.
Column: L1, C-18 RP column

DETAILED DESCRIPTION OF THE INVENTION

The inventors have found that Letrozole can be regioselectively synthesized using new processes for the preparation of the pure intermediate 4-[(1-(1,2,4-triazolyl)-methyl]benzonitrile (III) using novel salts and/or specific reaction conditions for the preparation of (III). The Letrozole thus obtained is surprisingly substantially free from the regioisomeric impurity (II) and is a major advance over the various processes described in the prior art discussed above.

Therefore, the present invention provides a simple, convenient and inexpensive method for the preparation of highly pure intermediate 4-[(1-(1,2,4-triazolyl)-methyl]benzonitrile (III), Letrozole and their pharmaceutically acceptable salts. The products obtained from the processes of the present invention are surprisingly very pure without the need for cumbersome purification techniques, such as column chromatography. In particular, the present invention provides Letrozole, 4-[(1-(1,2,4-triazolyl)methyl]benzonitrile (III) and their salts, substantially free of regioisomeric impurities.

The present invention provides a process for the preparation of 4-[(1-(1,2,4-triazolyl)methyl]benzonitrile (III) substantially free of its isomeric impurity (V) and Letrozole substantially free of its isomeric impurity (II, Impurity A as mentioned in USP pharmacopoeia specifications).

Preferred aspects of the present invention provide a commercially viable process for the preparation of pure intermediate 4-[(1-(1,2,4-triazolyl)methyl]benzonitrile (III) having a chemical purity of more than 99.5% by HPLC, preferably more than 99.6%, preferably more than 99.7%, preferably more than 99.8%, and most preferably more than 99.9%, which is also substantially free of regioisomeric impurity (V).

Figure 1:
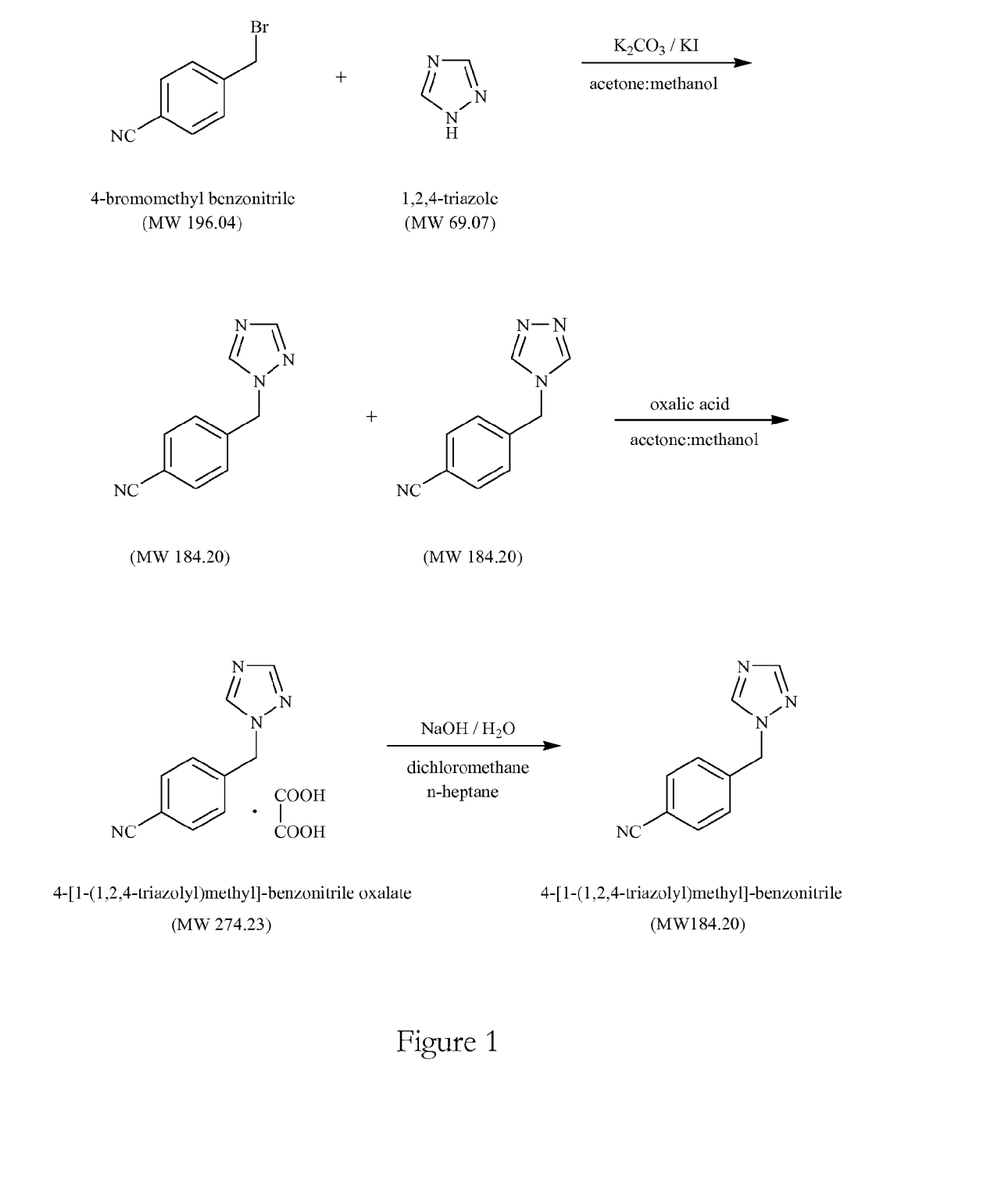
FIG. 1: Synthetic scheme for the synthesis of 4-[(1-(1,2,4-triazolyl)methyl]benzonitrile (III).

A particularly preferred process for the preparation of intermediate 4-[(1-(1,2,4-triazolyl)methyl]benzonitrile (III) is illustrated in FIG. 1.

A particularly preferred aspect of the present invention provides a method for the synthesis of the intermediate 4-[(1-(1,2,4-triazolyl)methyl]benzonitrile (III) comprising one or more of the following steps:
(a) Preparing a solution of 4-bromomethylbenzonitrile in polar solvents such as aliphatic alcohols (preferably methanol) and dialkyl ketones (preferably acetone) or their mixture, and adding potassium carbonate and potassium iodide;
(b) Slow addition of 1,2,4-triazole dissolved in polar solvents such as aliphatic alcohols (preferably methanol) and dialkyl ketones (preferably acetone) or their mixture, into the reaction mixture at 20 to 35° C.;
(c) Stirring of the reaction mixture at 20 to 35° C. until completion of the reaction;
(d) Filtration of potassium carbonate and potassium iodide and removal of the solvent by distillation;
(e) Addition of water to the residue and extraction of the crude 4-[(1-(1,2,4-triazolyl)methyl]benzonitrile dissolved in the aqueous layer with a solvent such as dichloromethane (DCM);
(f) Removal of the DCM to afford crude 4-[(1-(1,2,4-triazolyl)methyl]-benzonitrile;
(g) Preparation of an organic acid salt, preferably the oxalate salt, of crude 4-[(1-(1,2,4-triazolyl)methyl]benzonitrile in a polar solvent such as methanol or acetone or a mixture of both;
(h) Liberation of the free base of the oxalate salt by its treatment with an aqueous solution of a base, such as sodium hydroxide, and isolation of the liberated base from water by filtration;
(i) Dissolving the purified base of the isolated solid in dichloromethane and removal of the insoluble sodium salt of the organic acid by filtration; and
(j) Isolation of the purified 4-[(1-(1,2,4-triazolyl)methyl]benzonitrile as a white solid by the removal of solvent from the filtered dichloromethane layer and the addition of a non-polar solvent, such as a hydrocarbon, preferably n-heptane.

Figure 2:
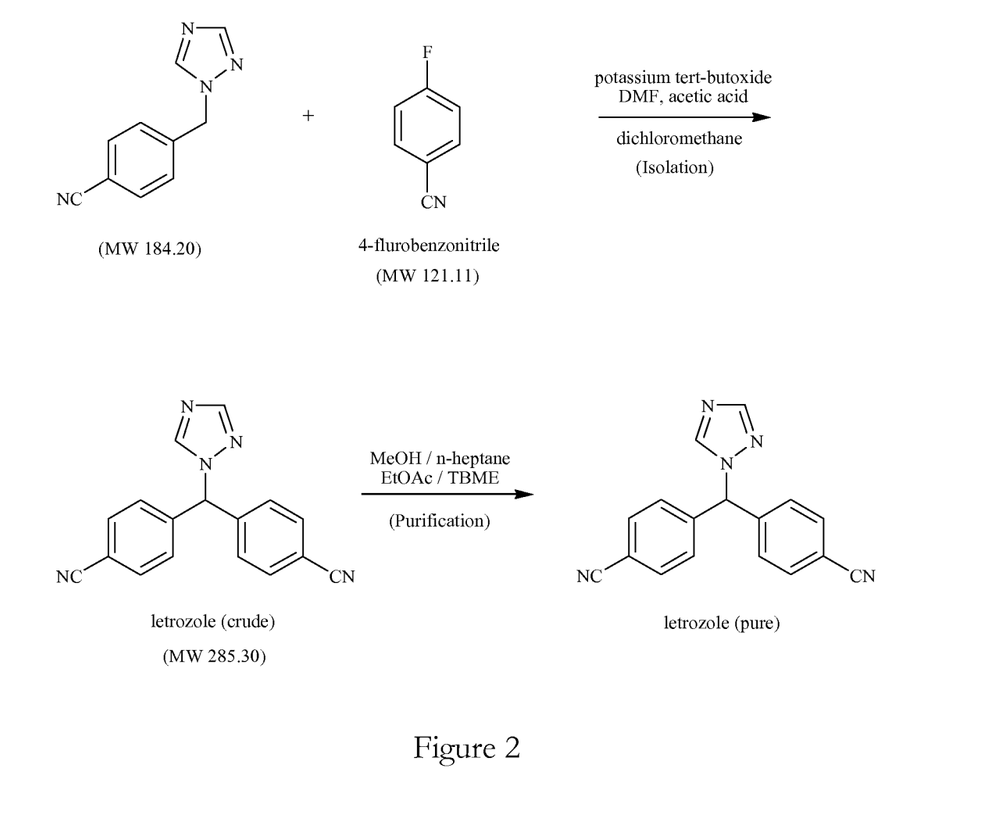
FIG. 2: Synthetic scheme for the synthesis of Letrozole (I) from 4-[(1-(1,2,4-triazolyl)methyl]benzonitrile (III).

A particularly preferred process for the preparation of Letrozole (I) is illustrated in FIG. 2.

A particularly preferred process for the preparation of Letrozole comprises one or more of the following steps:
(a) Dissolving potassium tertiary butoxide in dimethylformamide;
(b) Addition of 4-[(1-(1,2,4-triazolyl)methyl]benzonitrile solution in dimethylformamide into a potassium tertiary butoxide solution in a solvent such as dimethylformamide, preferably at a temperature of −5 to −15° C.;
(c) Mixing the reaction mixture with a 4-fluorobenzonitrile solution in dimethylformamide, preferably at the same temperature as in step (b);
(d) After completion of the reaction, the addition of a water immiscible solvent such as dichloromethane followed by the addition of an organic acid, preferably acetic acid, and removal of the potassium acetate by filtration of the reaction mixture;
(e) Washing of the organic layer with water and then removal of the solvent;
(f) Dissolving the residue in a polar solvent such as an alcohol, preferably methanol or 2-propanol, and addition of a non-polar solvent such as n-heptane;
(g) Isolation of the solid Letrozole with >99% purity on HPLC;
(h) Purification of Letrozole using a solvent, such as an alkyl ester of an alkyl carboxylic acid, e.g. ethyl acetate, and a non polar solvent, preferably alkanes such as n-heptane or dialkyl ethers such as tert-butyl methyl ether, to afford pure Letrozole with HPLC purity 99.9% or higher.

In a preferred embodiment the solid obtained in step (h) is dried at a temperature between about 30-60° C., more preferably at 40-60° C. and most preferably at 50-55° C. under reduced pressure, preferably for approximately 2 to 6 hours.

Various prior art processes described the reaction of 4-bromomethylbenzonitrile with 1,2,4-triazole, with a suitable base and solvent at reflux temperature. The present inventors observed that when the reaction was carried out in methanol or acetone individually, the refluxing was required to complete the reaction however, it has been surprisingly found that by using a mixture of solvents such as a ketone and an alcohol (for example acetone and methanol), after an appropriate adjustment of the solvent ratio, quantity of base (e.g. potassium carbonate) and catalyst (e.g. potassium iodide), the reaction can be completed at ambient temperature i.e. at 20 to 35° C. It was also surprisingly found that the regioselectivity of the reaction was much higher. The unwanted regioisomer (V) was found in less than 12% in the crude product as compared with prior art processes wherein the regioisomer (V) was formed in an amount between 15 to 20% or higher.

Various purification methods such as solvent purification and selective preparations of hydrochloride salts were described in the prior art but these methods could not make the intermediate (III) highly pure. The inventors have surprisingly found that when the salt of the crude 4-[(1-(1,2,4-triazolyl)methyl]benzonitrile (III) was prepared with relatively weak acids, such as various organic acids like carboxylic acids, and sulfonic acids like methane sulfonic acid or para-toluene sulfonic acids, it was observed that very high purity could be achieved. Dicarboxylic acid salts, especially oxalic acid salt, are most preferred for achieving the desired regioisomeric and chemical purity of 4-[(1-(1,2,4-triazolyl)methyl]benzonitrile (III) with good yield.

The processes according to the present invention may be used for the preparation of the organic acid salt intermediates with the following acids: formic acid; acetic acid; propionic acid; butyric acid; tartaric acid; oxalic acid; succinic acid; fumaric acid; methane sulfonic acid and p-toluenesulfonic acid. The most preferred acid is oxalic acid.

Furthermore, the present invention provides methods of preparation of 4-[(1-(1,2,4-triazolyl)methyl]benzonitrile which have advantageous combinations of features not described previously in the prior art. The main advantages are:

1) Reaction of 4-bromomethylbenzonitrile with 1,2,4-triazole at ambient temperature between 20 to 40° C., preferably between 25 to 35° C.
2) Fast completion of the reaction in two to four hours which saves reactor occupancy time and increases productivity.
3) Simple work up of the reaction mixture for the isolation of the crude 4-[(1-(1,2,4-triazolyl)methyl]benzonitrile.
4) Purification of the crude 4-[(1-(1,2,4-triazolyl)methyl]benzonitrile by salt formation with organic sulfonic acids or other organic acids, preferably aliphatic or aromatic mono-carboxylic or di-carboxylic acids, most preferably oxalic acid.
5) Selective separation of 4-[(1-(1,2,4-triazolyl)methyl]benzonitrile from its corresponding regioisomer 4-[(1-(1,3,4-triazolyl)methyl]benzonitrile by a specific choice of solvents, preferably the same as used for the preparation and isolation of the organic acid salt.
6) Hydrolysis of the organic acid salt and liberation of the purified base by using water as solvent to obtain 4-[(1-(1,2,4-triazolyl)methyl]benzonitrile with high chemical purity, substantially free from regioisomeric impurity.
7) Preparation of the intermediate 4-[(1-(1,2,4-triazolyl)methyl]benzonitrile in crystalline anhydrous form having at least 3 or seven XRPD peaks at 4.91, 7.60, 8.70, 11.80, 12.65, 15.80, 16.74, 17.31, 18.47, 20.13, 21.22, 21.73, 22.88, 23.26, 24.10, 26.01, 28.25 and 29.40 degrees 2-Theta.
8) Preparation of the intermediate 4-[(1-(1,2,4-triazolyl)methyl]benzonitrile in crystalline anhydrous form having a single endothermic peak at 77 to 79° C. in differential scanning calorimetry (DSC analysis).
9) Use of the intermediate 4-[(1-(1,2,4-triazolyl)methyl]benzonitrile for the preparation of Letrozole having a high chemical purity of 99.9% or higher by HPLC, without having any individual known or unknown impurity higher than 0.1%.

The reagents and solvents illustrated in FIGS. 1 and 2 are merely illustrative of the present invention and the reaction schemes are not limited by these reagents and solvents. Any suitable alternatives can be used.

The processes of the present invention provide a commercially viable process for the preparation of Letrozole resulting in a greater than 60% molar overall yield and HPLC purity of 99.90% or higher, preferably 99.95% or higher, and more preferably 99.98% or higher.

If required, Letrozole can be prepared from intermediate (III), prepared according to an aspect of the present invention, by its reaction with 4-fluorobenzonitrile (IV) in the presence of strong base like potassium tert-butoxide, as described in U.S. Pat. No. 4,978,672 and other prior art process described above.

Preferably, the final purification of Letrozole is carried out by using a solvent mixture having a solvent derived from aliphatic acid ester such as ethyl acetate, isopropyl acetate or amyl acetate, and non polar solvents such as ethers, preferably ethyl ether or tertiary butyl methyl ether (TBME). Preferably, the aliphatic acid ester is ethyl acetate and the ether is tertiary butyl methyl ether (TBME).

Preferably, the Letrozole is prepared having a purity of more than 99.8% by HPLC with isomeric impurity less than 0.1%.

Preferably, the products are obtained in a yield of 70% or more, preferably 80% or more, preferably 90% or more, preferably 95% or more. Preferably, the Letrozole is obtained substantially free of chemical impurities.

Preferably, the Letrozole is obtained on a commercial scale, preferably in batches of 1 kg or more, 10 kg or more, 100 kg or more, 500 kg or more, or 1000 kg or more.

The pharmaceutical composition according to the eighteenth aspect of the present invention can be a solution or suspension form, but is preferably a solid oral dosage form. Preferred dosage forms in accordance with the invention include tablets, capsules and the like which, optionally, may be coated if desired. Tablets can be prepared by conventional techniques, including direct compression, wet granulation and dry granulation. Capsules are generally formed from a gelatine material and can include a conventionally prepared granulate of excipients in accordance with the invention. The pharmaceutical composition according to the present invention typically comprises one or more conventional pharmaceutically acceptable excipient(s) selected from the group comprising of a fillet, a binder, a disintegrant and a lubricant, and optionally further comprises at least one excipient selected from colouring agents, adsorbents, surfactants, film formers and plasticizers.

As described above, the pharmaceutical composition of the present invention typically comprises one or more fillers, such as microcrystalline cellulose, lactose, sugars, starches modified starches, mannitol, sorbitol and other polyols, dextrin, dextran or maltodextrin; one or more binders, such as lactose, starches, modified starch, maize starch, dextrin, dextran, maltodextrin, microcrystalline cellulose, sugars, polyethylene glycols, hydroxypropyl cellulose, hydroxypropyl methylcellulose, ethylcellulose, hydroxyethyl cellulose, methylcellulose, carboxymethyl cellulose, gelatin, acacia gum, tragacanth, polyvinylpyrrolidone or crospovidone; one or more disintegrating agents such as croscarmellose sodium, cross-linked polyvinylpyrrolidone, crospovidone, cross-linked carboxymethyl starch, starches, microcrystalline cellulose or polyactylin potassium; and one or more different glidants or lubricants such as magnesium stearate, calcium stearate, zinc stearate, calcium behenate, sodium stearyl fumarate, talc, magnesium trisilicate, stearic acid, palmitic acid, carnauba wax or silicon dioxide.

If required, the pharmaceutical composition of the present invention may also include surfactants and other conventional excipients.

If the solid pharmaceutical formulation is in the form of coated tablets, the coating may be prepared from at least one film-former such as hydroxypropyl methylcellulose, hydroxypropyl cellulose or methacrylate polymers which optionally may contain at least one plasticizer such as a polyethylene glycol, dibutyl sebacate, or triethyl citrate, and other pharmaceutical auxiliary substances conventional for film coatings, such as pigments, fillers and others.

A further aspect of the present invention provides the use of a pharmaceutical composition according to any preceding aspect of the present invention in the manufacture of a medicament for the treatment of cancer, in particular for the treatment of breast cancer in post menopausal women.

The details of the invention, its objects and advantages are explained hereunder in greater detail in the following non-limiting examples.

EXAMPLES

Example 1

4-[(1-(1,2,4-triazolyl)methyl]benzonitrile (III)

Potassium carbonate (70 g, 0.507 mole) and potassium iodide (8.4 g, 0.051 mole) were added to a solution of 4-bromomethylbenzonitrile (100 g, 0.510 mole) in acetone (500 ml). To this reaction mixture, a solution of 1,2,4-triazole (35 g, 0.507 mole) in methanol (500 ml) was slowly added under nitrogen at 25 to 35° C. over a period of 1 hour. The reaction mixture was stirred for a further two to four hours and, after completion of the reaction, the solid was filtered and the filtrate was concentrated by distillation at 40 to 45° C. under reduced pressure. Water (2000 ml) was added to the residue and the pH of reaction mixture was adjusted to between 6 and 7 with acetic acid (3 to 4 ml). The aqueous layer was extracted with dichloromethane (2000 ml) and the organic extract was washed with water (200 ml) and the organic solvent was removed by distillation at 40 to 45° C. under reduced pressure to afford 4-[(1-(1,2,4-triazolyl)methyl]-benzonitrile (III) as a crude residue.

A solution of oxalic acid dihydrate (68 g, 0.540 moles) in an equal volume (50:50) mixture of acetone and methanol (300 ml) was prepared and added to a solution of the crude residue in an equal volume (50:50) mixture of acetone and methanol (100 ml) under stirring at 25-30° C. After stirring for a further 30 minutes, the reaction mixture was cooled at 10 to 15° C. and then filtered to afford the oxalate salt of 4-[(1-(1,2,4-triazolyl)methyl]-benzonitrile. The solid was washed with an equal volume mixture of acetone and methanol (50 ml) and dried under suction.

The solid oxalate salt obtained was suspended in water (400 ml) and its pH was made alkaline (pH 7 to 8) by slow addition of a sodium hydroxide solution (10% w/V, ~200 ml) under stirring. The reaction mass was cooled at 10 to 15° C., filtered and the isolated solid was washed with water and dried under suction. The isolated solid was then dissolved in dichloromethane (1000 ml) and insoluble sodium oxalate was removed by filtration. The clear solution was concentrated until approximately 90% of the solvent was removed and n-heptane (120 ml) was added to the residue under stirring. The solid obtained was filtered and dried under suction. The product was dried at 45 to 50° C. at reduced pressure to afford 4-[(1-(1,2,4-triazolyl)methyl]benzonitrile (III) as a pure, off-white, free flowing solid. The product is characterised as the novel anhydrous crystalline 4-[(1-(1,2,4-triazolyl)methyl]-benzonitrile (III) with XRPD as in FIG. 3, DSC as in FIG. 4 and TGA as in FIG. 5.

Yield: 45.5 g (48.5% molar from 4-bromomethylbenzonitrile)

HPLC Purity: 99.8%

The regioisomeric impurity (V) was present at less than 0.10% (by area normalization).

Example 2

Letrozole (I)

A solution of the pure 4-[(1-(1,2,4-triazolyl)methyl]benzonitrile (100 g, 0.543 mole), obtained as in Example 1, in N,N-dimethylformamide (200 ml) was slowly added to a solution of potassium tertiary butoxide (182.9 g, 1.63 mole) in N,N-dimethyl-formamide (400 ml) under a nitrogen atmosphere whilst the temperature was maintained at −15 to −20° C. After 30 minutes stirring, a solution of 4-fluorobenzonitrile (IV) (65.8 g, 0.543 mole) in N,N-dimethylformamide (50 ml) was slowly added at the same temperature and the reaction mixture was stirred until completion of the reaction. Acetic acid (200 ml) was then added to the mixture at −10 to −15° C. and the pH of the mixture was adjusted to between about 5 to 6. After stirring for 1 hour, dichloromethane (1500 ml) was added to the mixture and the resultant mixture was filtered to remove impurities such as potassium acetate.

The clear filtrate was washed with water five times (total 5000 ml) and then concentrated under reduced pressure. Methanol (200 ml) was added to the residual semi-solid mass, followed by n-heptane (500 ml). The mixture was stirred first at 20 to 25° C. followed by cooling to 10 to 15° C. The isolated solid was filtered and dried under suction. The solid was dissolved in ethyl acetate (1500 ml) by heating and the clear solution was filtered and concentrated to 500 ml by distillation under reduced pressure. Tert-butyl methyl ether (TBME, 500 ml) was added to this residual solution and the mixture was cooled at 10 to 15° C. The precipitated solid was filtered, washed with TBME and dried under suction before being dried in a vacuum drier at 50 to 55° C. under low pressure to afford pure Letrozole (I) as a white to off-white solid.

Yield: 95 g (62% molar)

HPLC purity: 99.9% (by area normalization).

The regioisomeric impurity (II) could not be detected.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. An acid addition salt of 4-[1-(1,2,4-triazolyl)methyl] benzonitrile (III), wherein the acid is butyric, formic or oxalic acid.

2. A process for preparing a salt according to claim 1, comprising mixing 4-[1-(1,2,4-triazolyl)methyl]benzonitrile (III) with the acid in a solvent system.

3. A process according to claim 2, wherein,
the solvent system comprises one or more solvents selected from straight chain or branched aliphatic ketones and aliphatic $C_1$ to $C_4$ alcohols, or mixtures thereof.

4. An acid addition salt of 4-[1-(1,2,4-triazolyl)methyl]benzonitrile (III), wherein the acid is butyric, formic or oxalic acid with HPLC purity of equal to or more than 99.8%.

5. An acid addition salt of 4-[1-(1,2,4-triazolyl)methyl]benzonitrile (III), wherein the acid is butyric, formic or oxalic acid substantially free of the regioisomeric impurity 4-[1-(1,3,4-triazolyl)-methyl]benzonitrile (V) or salts thereof.

6. The acid addition salt of 4-[1-(1,2,4-triazolyl)methyl]benzonitrile (III) according to claim 5, with HPLC purity of equal to or more than 99.8%.

7. The process of claim 2, wherein the solvent system comprises one or more solvents selected from straight chain or branched aliphatic ketones and aliphatic C1 to C4 alcohols, or mixtures thereof, wherein the ketone is selected from acetone, methyl ethyl ketone and methyl isopropyl ketone, or mixtures thereof.

8. The process of claim 2, wherein the solvent system comprises one or more solvents selected from straight chain or branched aliphatic ketones and aliphatic C1 to C4 alcohols, or mixtures thereof, wherein the alcohol is selected from methanol, ethanol, 1-propanol, 2-propanol, 1-butanol and tertiary butanol, or mixtures thereof.

9. The process of claim 2, wherein the solvent system comprises acetone and methanol.

10. The process of claim 2, wherein the solvent system comprises acetone and methanol, wherein the ratio of acetone:methanol in the solvent system is about 95:5, about 80:20, about 60:40, or about 50:50 by volume.

11. A method for preparing 4-[1-(1,2,4-triazolyl)methyl]benzonitrile (III), said method comprising purifying the acid addition salt of claim 1 and subsequently liberating the 4-[1-(1,2,4-triazolyl)methyl]benzonitrile (III) from the purified salt.

12. A process according to claim 11, wherein the salt is purified by crystallisation from a solvent system.

13. The process according to claim 12, wherein the solvent system comprises one or more solvents selected from straight chain or branched aliphatic ketones and aliphatic C1 to C4 alcohols, or mixtures thereof, wherein the ketone is selected from acetone, methyl ethyl ketone and methyl isopropyl ketone, or mixtures thereof.

14. The process according to claim 12, wherein the solvent system comprises one or more solvents selected from straight chain or branched aliphatic ketones and aliphatic C1 to C4 alcohols, or mixtures thereof, wherein the alcohol is selected from methanol, ethanol, 1-propanol, 2-propanol, 1-butanol and tertiary butanol, or mixtures thereof.

15. The process according to claim 12, wherein the solvent system comprises acetone and methanol.

16. The process according to claim 12, wherein the solvent system comprises acetone and methanol, wherein the ratio of acetone:methanol in the solvent system is about 95:5, about 80:20, about 60:40, or about 50:50 by volume.

* * * * *